United States Patent [19]
Gorbach

[11] Patent Number: 6,083,526
[45] Date of Patent: *Jul. 4, 2000

[54] USE OF ISOFLAVONOIDS IN THE TREATMENT OR PREVENTION OF POSTPARTUM DEPRESSION

[76] Inventor: Sherwood L. Gorbach, 31 Perry La., Weston, Mass. 02193

[*] Notice: This patent issued on a continued prosecution application filed under 37 CFR 1.53(d), and is subject to the twenty year patent term provisions of 35 U.S.C. 154(a)(2).

[21] Appl. No.: 08/861,485

[22] Filed: May 22, 1997

[51] Int. Cl.[7] .............. A61F 13/00; A61K 9/70; A61K 9/20; A61K 47/00
[52] U.S. Cl. .......... 424/439; 424/449; 424/451; 424/464; 424/489
[58] Field of Search ............... 424/449, 195.1, 424/439, 464, 465, 451, 489

[56] References Cited

U.S. PATENT DOCUMENTS

| | | | |
|---|---|---|---|
| 5,516,528 | 5/1996 | Hughes | 424/464 |
| 5,569,459 | 10/1996 | Shlyankevich | 424/195.1 |
| 5,589,182 | 12/1996 | Tashiro | 424/423 |

FOREIGN PATENT DOCUMENTS

WO94/23716  10/1994  WIPO .

OTHER PUBLICATIONS

Gregoire et al. Transdermal oestrogen for treatment of severe postnatal depression. The Lancet 347: 930–33, 1996.
Klaiber et al. Estrogen therapy for severe persistent depressions in women. Arch. Gen. Psychiatry 36: 550–54, 1979.
Murray. Oestrogen and postnatal depression. The Lancet 347: 918–19, 1996.
Sichel et al. Prophylactic estrogen in recurrent postpartum affective disorder. Biol. Psychiatry 38: 814–18, 1995.

*Primary Examiner*—Thurman K. Page
*Assistant Examiner*—Sharon Howard
*Attorney, Agent, or Firm*—Clark & Elbing LLP

[57] ABSTRACT

A method of treating or preventing postpartum depression by administration of a composition containing one or more purified, naturally-occurring isoflavonoids.

18 Claims, No Drawings

USE OF ISOFLAVONOIDS IN THE TREATMENT OR PREVENTION OF POSTPARTUM DEPRESSION

BACKGROUND OF THE INVENTION

The present invention relates to therapies for the prevention and treatment of postpartum depression, as well as other psychological disturbances that develop after childbirth.

It has long been recognized that psychological disturbances are very common in the postpartum period, usually beginning within 6 weeks after delivery. The psychological conditions can range from "maternity blues," which are usually mild, to a more severe depression, which is known to occur in fully 10% of postpartum women. Depression can have psychological effects that last for several months and occasionally even longer. A related concern is the impaired cognitive abilities and delayed social development that can be seen in the children of women who have experienced postpartum depression. At least a part of the explanation for postpartum depression is the changing hormone milieu in the woman's body following childbirth. Estrogen hormone achieves and maintains a high level during pregnancy and then drops precipitously within 48 hours after delivery to nearly the follicular level, which is the lowest level in a normally menstruating woman. This causes an acute estrogen withdrawal state, which could have effects on psychological and mental functioning. In this regard postpartum depression has been treated successfully with estrogen. In other reports estrogen has been administered immediately after childbirth to prevent recurrence of depression and other psychological disorders in women who are at risk of developing these problems in the postpartum period. Various antidepressant drugs, such as lithium, tricyclic compounds and serotonin-specific reuptake inhibitors (SSRI), have been used in postpartum depression with varying degrees of success. There is, however, concern about their side effects and their safety in breastfeeding women. Treatment with large doses of estrogen is also a concern in breastfeeding women. Safer, effective therapies for treating and preventing postpartum depression continue to be sought.

SUMMARY OF THE INVENTION

The invention features a method of treating or preventing postpartum depression in a woman who has recently given birth to a baby; the method involves administering to the woman, within six weeks (and preferably, within 24, or even 12, hours) a composition containing one or more purified isoflavonoids selected from the group consisting of genistein, daidzein, biochanin A, formononetin, O-desmethylangolensin, glycitin, and equol. Preferably, the composition is administered orally, providing a dosage of at least 20 mg of total isoflavonoid per serving. The orally-administerable composition can be a non-naturally occurring dietary product such as a convectionary bar, cereal, biscuit, or beverage. Alternatively, the composition can take the form of a medicament such as a pill, capsule, tablet, powder, or syrup, in which the total isoflavonoid is present in at least an amount of 20 mg per unit dose. Preferably, the dietary product or medicament is orally consumed by the patient once, twice, or three times per day, to provide a daily oral isoflavonoid dose of between 20 and 300 mg. Preferably, the oral ingestion of the composition is sufficient to produce a transient concentration in the bloodstream of the woman of at least 50 nm of total isoflavonoid per liter of blood. By "purified" isoflavonoid is meant an isoflavonoid in more concentrated form than occurs in plants.

The isoflavonoids can also be administered in the form of a topical medicament applied directly to the skin; the medicament is composed of a dermatologically acceptable base substance admixed with the isoflavonoids; preferably, the topically applied composition contains between 1 and 40 mg isoflavonoid per gram of base. In one embodiment, the medicament forms part of a transdermnal delivery system or patch, which is applied to the skin once, twice, or three times per day.

Other features and advantages of the invention will be apparent from the following Detailed Description thereof, and from the claims.

DETAILED DESCRIPTION

Isoflavonoids are naturally occurring substances, found primarily in soy beans. These compounds can also be found in high concentrations in red clover and in lower amounts in many other types of plants. An isoflavonoid-containing fraction useful in the invention can be extracted from a soy or plant product. It is preferred that the isoflavonoids be extracted and concentrated from soy bean or soy powder, but other plants such as clover can be used. Isoflavonoids are also available commercially in substantially pure form. The concentrated isoflavonoid is preferably included in a food carrier to form a dietary product. Any type of palatable carrier may be used, but as the isoflavonoid concentrate has a strong flavor, it is preferred that the carrier include suitable flavorings to impart a different, more palatable flavor. The dietary product may be any type of food product, e.g., a confectionary bar, biscuit, cereal, or beverage.

It is preferred that the dietary product contain at least 20 mg/serving total isoflavonoids. The isoflavonoid concentrate included in the dietary product preferably includes a blend of isoflavonoids with genistein, daidzein, biochanin A, formononetin, O-desmethylangolensin, glycitin, and equol; these may be administered alone or in combination. Preferably, a dietary product containing the preferred dosage of isoflavonoids is consumed at least once per day, more preferably 2, or 3 times per day for more severe symptoms, to provide a daily oral isoflavonoid dose of 20–300 mg, more preferably 30–75 mg.

The isoflavonoid also can be administered, preferably in similar dosages, in medicament form, e.g., mixed with a pharmaceutically acceptable carrier to form a pill, tablet, capsule or powder, or a liquid or syrup formulation. A topical medicament form can also be included in a transdermal delivery system or patch such as those that are well-known for the delivery of sustained doses of nicotine or estrogen.

When isoflavonoids are fed to healthy American adults, the absorption into the bloodstream is 10 to 20% of the amount consumed. This produces blood levels of isoflavonoids 200 to 2000 times higher than the levels of the most active natural estrogen in women, estradiol. It is known that the estrogenic activity of isoflavonoids is about 1000 to 10,000 lower than that of estrogen contained in estrogen replacement therapy. These determinations indicate that consumption of isoflavonoids in dosages of 20 to 50 mg per day provides blood levels with estrogenic activity in the range of that found with estrogen replacement therapy.

Isoflavonoids have similar chemical properties to estrogens, specifically they are poorly soluble in water but are readily soluble in alcohol or organic solvents. For topical application in a transdermal delivery system or patch, isoflavonoid is mixed in a conventional dermatologically acceptable base with ingredients such as alcohol, mineral oil, glyceryl monostearate, an ether complex of fatty acids, acetyl alcohol, lanolin, propylene glycol, stearyl alcohol, or sodium lauryl sulfate. The dose of isoflavonoid in the topical form is 1 to 40 mg per gram of the base.

Other embodiments are within the claims.

We claim:

1. A method of treating or preventing postpartum depression in a woman who has recently given birth to a baby, said method comprising administering to the woman, within six weeks of delivery, a composition comprising one or more purified isoflavonoids selected from the group consisting of genistein, daidzein, biochanin A, formononetin, O-desmethylangolensin, glycitin, and equol, in an amount sufficient to produce a transient concentration in the bloodstream of said woman of at least 50 nanomoles/l.

2. The method of claim 1 wherein said composition is administered orally, in a dosage of at least 20 mg of isoflavonoid per serving.

3. The method of claim 2 wherein said composition is administered once, twice, or three times per day.

4. The method of claim 1 wherein said composition is in the form of a non-naturally occurring dietary product.

5. The method of claim 4 wherein said isoflavonoid contains at least 20 mg/serving of said isoflavonoid.

6. The method of claim 4 wherein said dietary product is a confectionary bar.

7. The method of claim 4 wherein said dietary product is a cereal.

8. The method of claim 4 wherein said dietary product is a biscuit.

9. The method of claim 4 wherein said dietary product is a beverage.

10. The method of claim 1 wherein said composition is in the form of a pill, capsule tablet, powder, or syrup.

11. The method of claim 10 wherein said composition contains at least 20 mg/unit dose of isoflavonoid.

12. The method of claim 1, wherein said composition is administered beginning less than twenty-four hours postpartum, at a dose of at least 20 mg/day, for a period of at least five days.

13. The method of claim 10 wherein said composition is consumed orally by said patient once, twice, or three times a day.

14. The method of claim 1 wherein said composition is administered in the form of a topical medicament applied directly to the skin surface, said medicament comprising a dermatologically acceptable base substance carrying said isoflavonoid.

15. The method of claim 14 wherein said composition contains between 1 and 40 mg of isoflavonoid per gram of base.

16. The method of claim 14 wherein said medicament forms part of a transdermal delivery system or patch.

17. The method of claim 14 wherein said isoflavonoid is applied to the skin once, twice, or three times per day.

18. The method of claim 12, wherein said composition is administered less than twelve hours postpartum.

* * * * *